United States Patent
Bokil

(10) Patent No.: US 10,067,659 B2
(45) Date of Patent: Sep. 4, 2018

(54) SYSTEMS AND METHODS FOR DETERMINING ORIENTATION OF AN IMPLANTED LEAD

(71) Applicant: Boston Scientific Neuromodulation Corporation, Valencia, CA (US)

(72) Inventor: Hemant Bokil, Santa Monica, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 123 days.

(21) Appl. No.: 15/244,977

(22) Filed: Aug. 23, 2016

(65) Prior Publication Data

US 2017/0061627 A1   Mar. 2, 2017

Related U.S. Application Data

(60) Provisional application No. 62/209,001, filed on Aug. 24, 2015.

(51) Int. Cl.
  *G06K 9/00* (2006.01)
  *A61B 5/00* (2006.01)
  (Continued)

(52) U.S. Cl.
  CPC .............. *G06F 3/04845* (2013.01); *A61B 6/12* (2013.01); *A61B 90/39* (2016.02); *A61N 1/0534* (2013.01);
  (Continued)

(58) Field of Classification Search
  CPC . G06F 3/04845; G06F 3/04842; A61B 90/39; A61B 6/12; A61B 2090/3966; A61N 1/0534; A61N 1/0551; A61N 1/372; G16H 40/63; G06T 2207/10004; G06T 2200/24; G06T 7/73

USPC ....... 382/100, 128, 232, 233, 244, 247, 173; 345/418, 419, 424, 420, 581, 606, 427, 345/426, 423; 600/300, 407; 375/E7.001, E7.026, E7.076, E7.081
  See application file for complete search history.

(56) References Cited

U.S. PATENT DOCUMENTS 6,181,969 B1   1/2001   Gord
6,516,227 B1   2/2003   Meadows et al.
(Continued)

OTHER PUBLICATIONS

U.S. Appl. No. 62/408,392 filed Oct. 14, 2016.
(Continued)

*Primary Examiner* — Sheela C Chawan
(74) *Attorney, Agent, or Firm* — Lowe Graham Jones PLLC; Bruce E. Black

(57) ABSTRACT

A method and system for identifying a rotational orientation of an implanted electrical stimulation lead utilize radiological images of the lead. The lead has an asymmetric marker with a longitudinal band extending around a portion of the circumference of the lead. The method and system includes obtaining radiological images of the lead; generating an isosurface image from the radiological images and displaying the isosurface image on a display device, where the isosurface image comprises an image of the longitudinal band of the marker; identifying a bulge in the isosurface image corresponding the longitudinal band of the marker; and determining a rotational orientation of the lead based on the rotational orientation of the bulge in the isosurface image.

20 Claims, 4 Drawing Sheets

(51) Int. Cl.
*G06F 3/0484* (2013.01)
*A61B 6/12* (2006.01)
*A61N 1/05* (2006.01)
*A61N 1/372* (2006.01)
*A61B 90/00* (2016.01)
*G06T 7/73* (2017.01)
*G16H 40/63* (2018.01)

(52) U.S. Cl.
CPC .......... *A61N 1/0551* (2013.01); *A61N 1/372* (2013.01); *G06F 3/04842* (2013.01); *G06T 7/73* (2017.01); *A61B 2090/3966* (2016.02); *G06T 2200/24* (2013.01); *G06T 2207/10004* (2013.01); *G16H 40/63* (2018.01)

(56) References Cited

U.S. PATENT DOCUMENTS

| | | | |
|---|---|---|---|
| 6,609,029 | B1 | 8/2003 | Mann et al. |
| 6,609,032 | B1 | 8/2003 | Woods et al. |
| 6,741,892 | B1 | 8/2004 | Meadows et al. |
| 6,895,280 | B2 | 5/2005 | Meadows et al. |
| 7,244,150 | B1 | 7/2007 | Brase et al. |
| 7,437,193 | B2 | 10/2008 | Parramon et al. |
| 7,450,997 | B1 | 11/2008 | Pianca et al. |
| 7,650,184 | B2 | 1/2010 | Walter |
| 7,672,734 | B2 | 3/2010 | Anderson et al. |
| 7,761,165 | B1 | 7/2010 | He et al. |
| 7,783,359 | B2 | 8/2010 | Meadows |
| 7,792,590 | B1 | 9/2010 | Pianca et al. |
| 7,809,446 | B2 | 10/2010 | Meadows |
| 7,930,014 | B2 * | 4/2011 | Huennekens ......... A61B 6/504 382/159 |
| 7,949,395 | B2 | 5/2011 | Kuzma |
| 7,974,706 | B2 | 7/2011 | Moffitt et al. |
| 8,019,439 | B2 | 9/2011 | Kuzma et al. |
| 8,175,710 | B2 | 5/2012 | He |
| 8,224,450 | B2 | 7/2012 | Brase |
| 8,271,094 | B1 | 9/2012 | Moffitt et al. |
| 8,295,944 | B2 | 10/2012 | Howard et al. |
| 8,326,433 | B2 | 12/2012 | Blum et al. |
| 8,364,278 | B2 | 1/2013 | Pianca et al. |
| 8,391,985 | B2 | 3/2013 | McDonald |
| 8,473,061 | B2 | 6/2013 | Moffitt et al. |
| 8,571,665 | B2 | 10/2013 | Moffitt et al. |
| 8,675,945 | B2 | 3/2014 | Barnhorst et al. |
| 8,688,235 | B1 | 4/2014 | Pianca et al. |
| 8,792,993 | B2 | 7/2014 | Pianca et al. |
| 8,831,731 | B2 | 9/2014 | Blum et al. |
| 8,849,632 | B2 | 9/2014 | Sparks et al. |
| 8,958,615 | B2 | 2/2015 | Blum et al. |
| 9,037,256 | B2 | 5/2015 | Bokil et al. |
| 2003/0074011 | A1 * | 4/2003 | Gilboa .................... A61B 5/06 606/130 |
| 2007/0150036 | A1 | 6/2007 | Anderson |
| 2009/0187222 | A1 | 7/2009 | Barker |
| 2009/0204192 | A1 | 8/2009 | Carlton et al. |
| 2009/0276021 | A1 | 11/2009 | Meadows et al. |
| 2009/0287271 | A1 | 11/2009 | Blum et al. |
| 2009/0287272 | A1 | 11/2009 | Kokones et al. |
| 2009/0287273 | A1 | 11/2009 | Carlton et al. |
| 2010/0030298 | A1 | 2/2010 | Martens et al. |
| 2010/0076535 | A1 | 3/2010 | Pianca et al. |
| 2010/0268298 | A1 | 10/2010 | Moffitt et al. |
| 2011/0004267 | A1 | 1/2011 | Meadows |
| 2011/0005069 | A1 | 1/2011 | Pianca |
| 2011/0078900 | A1 | 4/2011 | Pianca et al. |
| 2011/0130803 | A1 | 6/2011 | McDonald |
| 2011/0130816 | A1 | 6/2011 | Howard et al. |
| 2011/0130817 | A1 | 6/2011 | Chen |
| 2011/0130818 | A1 | 6/2011 | Chen |
| 2011/0238129 | A1 | 9/2011 | Moffitt et al. |
| 2011/0257707 | A1 | 10/2011 | Kothandaraman |
| 2011/0313500 | A1 | 12/2011 | Barker et al. |
| 2012/0016378 | A1 | 1/2012 | Pianca et al. |
| 2012/0046710 | A1 | 2/2012 | DiGiore et al. |
| 2012/0046715 | A1 | 2/2012 | Moffitt et al. |
| 2012/0071949 | A1 | 3/2012 | Pianca et al. |
| 2012/0165911 | A1 | 6/2012 | Pianca |
| 2012/0197375 | A1 | 8/2012 | Pianca et al. |
| 2012/0203316 | A1 | 8/2012 | Moffitt et al. |
| 2012/0203320 | A1 | 8/2012 | DiGiore et al. |
| 2012/0203321 | A1 | 8/2012 | Moffitt et al. |
| 2012/0314919 | A1 | 12/2012 | Sparks et al. |
| 2012/0314924 | A1 | 12/2012 | Carlton et al. |
| 2012/0316615 | A1 | 12/2012 | DiGiore et al. |
| 2013/0039550 | A1 | 2/2013 | Blum et al. |
| 2013/0105071 | A1 | 5/2013 | DiGiore et al. |
| 2013/0116744 | A1 | 5/2013 | Blum et al. |
| 2013/0197424 | A1 | 8/2013 | Bedenbaugh |
| 2013/0197602 | A1 | 8/2013 | Pianca et al. |
| 2013/0267837 | A1 | 10/2013 | Schulte et al. |
| 2014/0039587 | A1 | 2/2014 | Romero |
| 2014/0122379 | A1 | 5/2014 | Moffitt et al. |
| 2014/0228921 | A1 | 8/2014 | Howard |
| 2014/0257428 | A1 | 9/2014 | Zhu |
| 2014/0276002 | A1 | 9/2014 | West et al. |
| 2014/0353001 | A1 | 12/2014 | Romero et al. |
| 2014/0358207 | A1 | 12/2014 | Romero |
| 2014/0358208 | A1 | 12/2014 | Howard et al. |
| 2014/0358209 | A1 | 12/2014 | Romero et al. |
| 2014/0358210 | A1 | 12/2014 | Howard et al. |
| 2014/0371819 | A1 | 12/2014 | Goetz et al. |
| 2015/0018915 | A1 | 1/2015 | Leven |
| 2015/0045864 | A1 | 2/2015 | Howard |
| 2015/0051681 | A1 | 2/2015 | Hershey |
| 2015/0066111 | A1 | 3/2015 | Blum et al. |
| 2015/0066120 | A1 | 3/2015 | Govea |
| 2015/0151113 | A1 | 6/2015 | Govea et al. |
| 2015/0157851 | A1 | 6/2015 | Sefkow et al. |
| 2016/0030749 | A1 | 2/2016 | Carcieri et al. |
| 2016/0228692 | A1 | 8/2016 | Steinke et al. |
| 2017/0056678 | A1 | 3/2017 | Bokil |
| 2017/0061627 | A1 | 3/2017 | Bokil |

OTHER PUBLICATIONS

International Search Report and Written Opinion for PCT/US2016/048225 dated Nov. 16, 2016.

U.S. Appl. No. 15/783,807 filed Oct. 13, 2017.

* cited by examiner

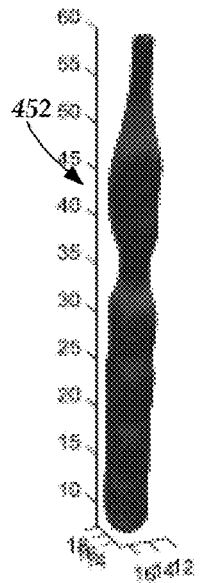
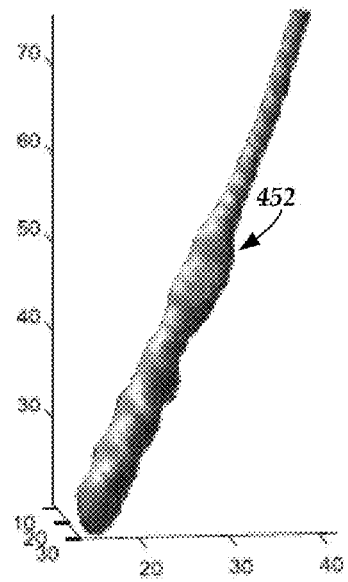
Fig. 4A  Fig. 4B
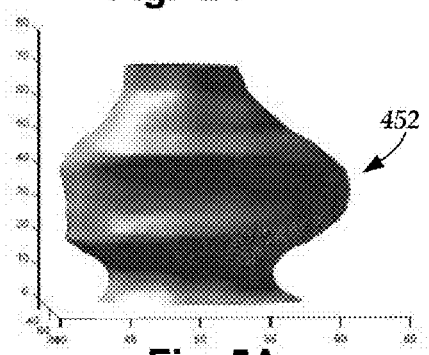
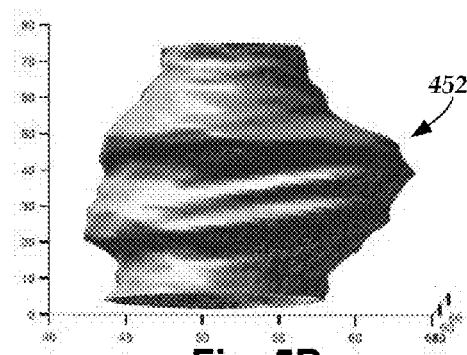
Fig. 5A  Fig. 5B
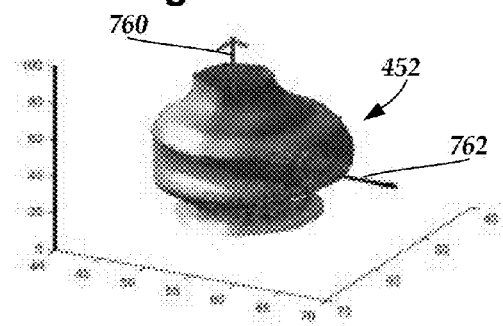
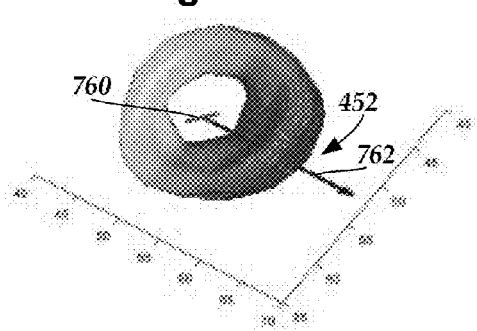
Fig. 7A  Fig. 7B

SYSTEMS AND METHODS FOR DETERMINING ORIENTATION OF AN IMPLANTED LEAD

CROSS-REFERENCE TO RELATED APPLICATIONS

This application claims the benefit under 35 U.S.C. § 119(e) of U.S. Provisional Patent Application Ser. No. 62/209,001, filed Aug. 24, 2015, which is incorporated herein by reference.

FIELD

The present invention is directed to the area of implantable electrical stimulation systems and methods of making and using the systems. The present invention is also directed to systems and methods for determining the orientation of an implanted electrical stimulation lead.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Stimulation of the brain, such as deep brain stimulation, can be used to treat a variety of diseases or disorders.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is a method for identifying a rotational orientation of an implanted electrical stimulation lead. The lead includes a lead body, segmented electrodes disposed along a distal portion of the lead body, and an asymmetric marker disposed along the distal portion of the lead body. The marker includes a longitudinal band that extends around a portion of a circumference of the lead body and defines a marker window extending around a remainder of the circumference of the lead body and opposite the longitudinal band. The asymmetric marker and lead body are formed of different materials that are distinguishable from each other in the radiological images and each segmented electrode extends around a portion of a circumference of the lead body. The method includes obtaining radiological images of the lead; generating an isosurface image from the radiological images and displaying the isosurface image on a display device, where the isosurface image comprises an image of the longitudinal band of the marker; identifying a bulge in the isosurface image corresponding the longitudinal band of the marker; and determining a rotational orientation of the lead based on the rotational orientation of the bulge in the isosurface image.

In at least some embodiments, the method further includes displaying, on the display device, a model of at least the distal portion of the lead oriented along the determined rotational orientation. In at least some embodiments, displaying a model comprises displaying the model of at least the distal portion of the lead and including models of the segmented electrodes of the lead.

In at least some embodiments, the method further includes rotating the isosurface image on the display device in response to a user command. In at least some embodiments, rotating the isosurface image comprises continuously rotating the isosurface image in response to a user command and stopping the rotation in response to a user command. In at least some embodiments, rotating the isosurface image comprises rotating the isosurface image about an axis selected by the user.

In at least some embodiments, determining a rotational orientation comprises placing an orientation axis on the isosurface image on the display device in response to a user command. In at least some embodiments, the method further includes modifying a direction of the orientation axis in response to user input. In at least some embodiments, the method further includes receiving an isovalue from a user input and generating another isosurface image based on the isovalue.

Another embodiment is a system for identifying a rotational orientation of an implanted electrical stimulation lead. The lead includes a lead body, segmented electrodes disposed along a distal portion of the lead body, and an asymmetric marker disposed along the distal portion of the lead body. The marker includes a longitudinal band that extends around a portion of a circumference of the lead body and defines a marker window extending around a remainder of the circumference of the lead body and opposite the longitudinal band. The asymmetric marker and lead body are formed of different materials that are distinguishable from each other in the radiological images and each segmented electrode extends around no more than 50% of a circumference of the lead body. The system includes a display device and a computer processor coupled to the display device and configured and arranged to perform the following actions: receiving radiological images of the lead; generating an isosurface image from the radiological images, where the isosurface image comprises an image of the longitudinal band of the marker; displaying the isosurface image on the display device; in response to a user command, rotating, on the display device, the isosurface about at least one axis; in response to a user command, displaying, on the display device, a user-selected orientation axis on the isosurface image; and, in response to a user command, displaying, on the display device, a model of at least the distal portion of the lead oriented along the orientation axis.

In at least some embodiments, the actions further include, in response to user input of an isovalue, generating another isosurface image based on the isovalue. In at least some embodiments, the actions further include displaying, on the display device, a slider control which the user can operate to input the isovalue. In at least some embodiments, the actions further include, in response to a user command, zooming into the isosurface image on the display device to magnify a portion of the isosurface image. In at least some embodiments, rotating the isosurface image includes continuously rotating the isosurface image in response to a user command and stopping the rotation in response to a user command. In at least some embodiments, rotating the isosurface image includes rotating the isosurface image includes rotating the isosurface image about an axis selected by the user.

In at least some embodiments, the actions further include displaying, on the display and relative to the model, at least one anatomical or physiological structure. In at least some embodiments, the actions further include displaying, on the display, a calculated distance between at least one of the electrodes of the lead and a one of the at least one anatomical or physiological structure. In at least some embodiments, the system further includes the lead. In at least some embodiments, the actions further include, in response to a user command, modifying, on the display device, a direction of the orientation axis.

Yet another embodiment is a computer-implemented method. The method includes receiving radiological images of a lead, the lead including a lead body, segmented electrodes disposed along a distal portion of the lead body, and an asymmetric marker disposed along the distal portion of the lead body and including a longitudinal band that extend around a portion of a circumference of the lead body and defines a marker window extending around a remainder of the circumference of the lead body and opposite the longitudinal band, where the asymmetric marker and lead body are formed of different materials that are distinguishable from each other in the radiological images, where each segmented electrode extends around no more than 50% of a circumference of the lead body. The method also includes generating an isosurface image from the radiological images, where the isosurface image includes an image of the longitudinal band of the marker; displaying the isosurface image on the display device; in response to a user command, rotating, on the display device, the isosurface about at least one axis; in response to a user command, displaying, on the display device, a user-selected orientation axis on the isosurface image; and, in response to a user command, displaying, on the display device, a model of at least the distal portion of the lead oriented along the orientation axis.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 4A is a schematic diagram of one embodiment of an isosurface image, according to the invention;

FIG. 4B is a schematic diagram of another embodiment of an isosurface image, according to the invention;

FIG. 5A is a schematic diagram of a portion of the isosurface image of FIG. 4A, according to the invention;

FIG. 5B is a schematic diagram of a portion of the isosurface image of FIG. 4B, according to the invention;

FIG. 7A is a schematic diagram of the portion of the isosurface image of FIG. 5A at a different angle, according to the invention;

FIG. 7B is a schematic diagram of a portion of the isosurface image of FIG. 5A from a top-down view, according to the invention;

DETAILED DESCRIPTION

The present invention is directed to the area of implantable electrical stimulation systems and methods of making and using the systems. The present invention is also directed to systems and methods for determining the orientation of an implanted electrical stimulation lead.

Suitable implantable electrical stimulation systems include, but are not limited to, a least one lead with one or more electrodes disposed on a distal end of the lead and one or more terminals disposed on one or more proximal ends of the lead. Leads include, for example, percutaneous leads, paddle leads, cuff leads, or any other arrangement of electrodes on a lead. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference. In the discussion below, a percutaneous lead will be exemplified, but it will be understood that the methods and systems described herein are also applicable to paddle leads and other leads.

A percutaneous lead for electrical stimulation (for example, deep brain or spinal cord stimulation) includes stimulation electrodes that can be ring electrodes, segmented electrodes that extend only partially around the circumference of the lead, or any other type of electrode, or any combination thereof. The segmented electrodes can be provided in sets of electrodes, with each set having electrodes circumferentially distributed about the lead at a particular longitudinal position. For illustrative purposes, the leads are described herein relative to use for deep brain stimulation, but it will be understood that any of the leads can be used for applications other than deep brain stimulation, including spinal cord stimulation, peripheral nerve stimulation, or stimulation of other nerves, muscles, and tissues.

Figure 1:
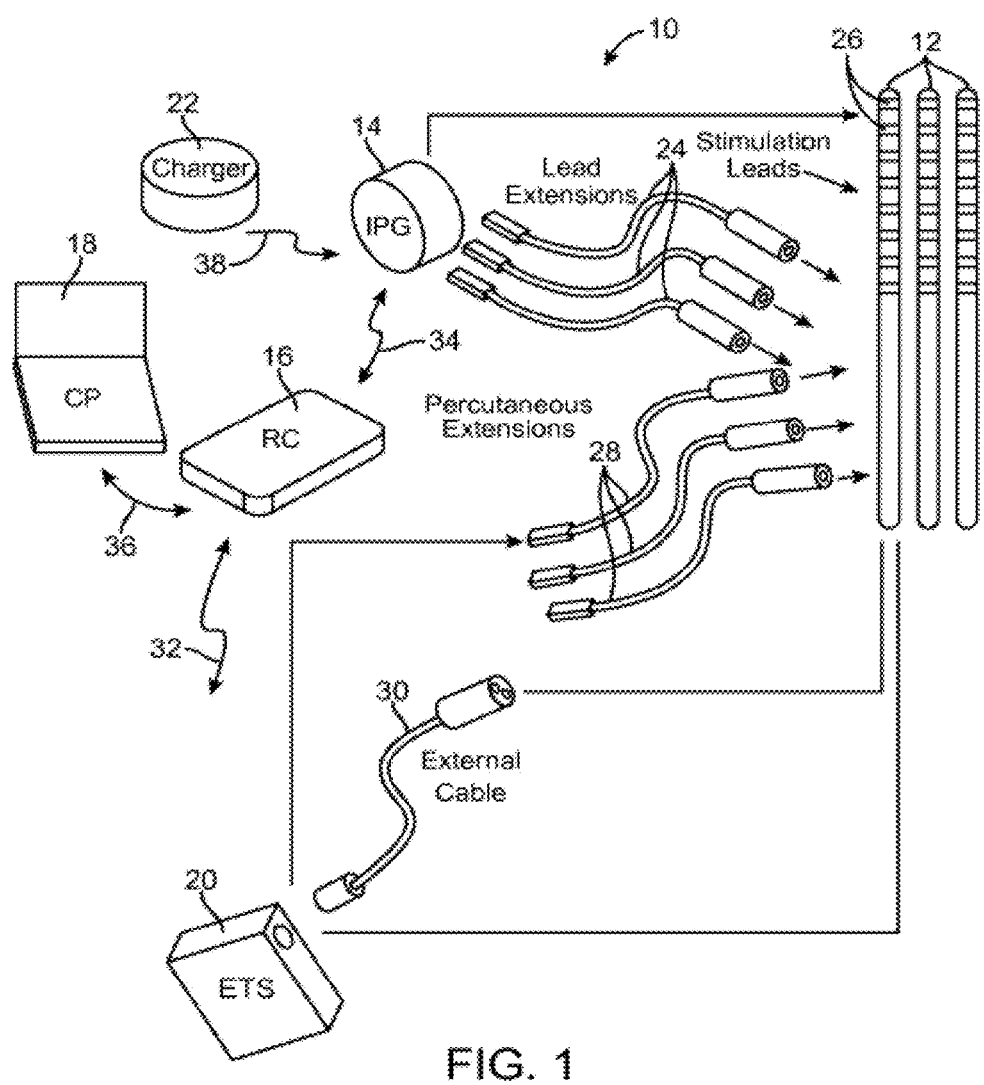
FIG. 1 is a schematic view of one embodiment of an electrical stimulation system, according to the invention.

Turning to FIG. 1, one embodiment of an electrical stimulation system 10 includes one or more stimulation leads 12 and an implantable pulse generator (IPG) 14. The system 10 can also include one or more of an external remote control (RC) 16, a clinician's programmer (CP) 18, an external trial stimulator (ETS) 20, or an external charger 22.

The IPG 14 is physically connected, optionally via one or more lead extensions 24, to the stimulation lead(s) 12. Each lead carries multiple electrodes 26 arranged in an array. The IPG 14 includes pulse generation circuitry that delivers electrical stimulation energy in the form of, for example, a pulsed electrical waveform (i.e., a temporal series of electrical pulses) to the electrode array 26 in accordance with a set of stimulation parameters. The implantable pulse generator can be implanted into a patient's body, for example, below the patient's clavicle area or within the patient's buttocks or abdominal cavity. The implantable pulse generator can have eight stimulation channels which may be independently programmable to control the magnitude of the current stimulus from each channel. In some embodiments, the implantable pulse generator can have more or fewer than eight stimulation channels (e.g., 4-, 6-, 16-, 32-, or more stimulation channels). The implantable pulse generator can have one, two, three, four, or more connector ports, for receiving the terminals of the leads.

The ETS 20 may also be physically connected, optionally via the percutaneous lead extensions 28 and external cable 30, to the stimulation leads 12. The ETS 20, which may have similar pulse generation circuitry as the IPG 14, also delivers electrical stimulation energy in the form of, for example, a pulsed electrical waveform to the electrode array 26 in accordance with a set of stimulation parameters. One difference between the ETS 20 and the IPG 14 is that the ETS 20 is often a non-implantable device that is used on a trial basis after the neurostimulation leads 12 have been implanted and prior to implantation of the IPG 14, to test the responsiveness of the stimulation that is to be provided. Any functions described herein with respect to the IPG 14 can likewise be performed with respect to the ETS 20.

The RC 16 may be used to telemetrically communicate with or control the IPG 14 or ETS 20 via a uni- or bi-directional wireless communications link 32. Once the IPG 14 and neurostimulation leads 12 are implanted, the RC 16 may be used to telemetrically communicate with or control the IPG 14 via a uni- or bi-directional communications link 34. Such communication or control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. The CP 18 allows a user, such as a clinician, the ability to program stimulation parameters for the IPG 14 and ETS 20 in the operating room and in follow-up sessions.

The CP 18 may perform this function by indirectly communicating with the IPG 14 or ETS 20, through the RC 16, via a wireless communications link 36. Alternatively, the CP 18 may directly communicate with the IPG 14 or ETS 20 via a wireless communications link (not shown). The stimulation parameters provided by the CP 18 are also used to program the RC 16, so that the stimulation parameters can be subsequently modified by operation of the RC 16 in a stand-alone mode (i.e., without the assistance of the CP 18).

For purposes of brevity, the details of the RC 16, CP 18, ETS 20, and external charger 22 will not be further described herein. Details of exemplary embodiments of these devices are disclosed in U.S. Pat. No. 6,895,280, which is expressly incorporated herein by reference. Other examples of electrical stimulation systems can be found at U.S. Pat. Nos. 6,181,969; 6,516,227; 6,609,029; 6,609,032; 6,741,892; 7,949,395; 7,244,150; 7,672,734; and 7,761,165; 7,974,706; 8,175,710; 8,224,450; and 8,364,278; and U.S. Patent Application Publication No. 2007/0150036, as well as the other references cited above, all of which are incorporated by reference.

Figure 2:
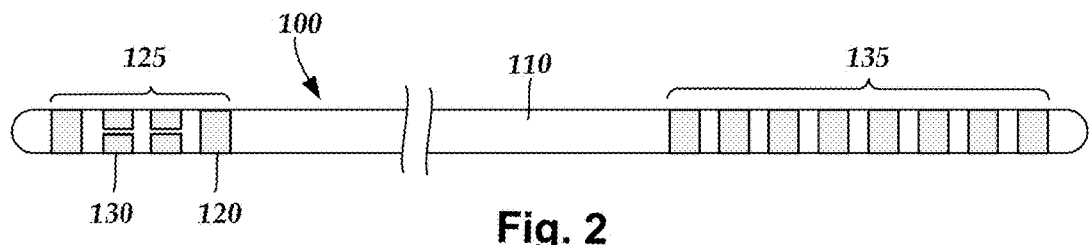
FIG. 2 is a schematic side view of one embodiment of an electrical stimulation lead, according to the invention.

FIG. 2 illustrates one embodiment of a lead 110 with electrodes 125 disposed at least partially about a circumference of the lead 110 along a distal end portion of the lead and terminals 135 disposed along a proximal end portion of the lead. The lead 110 can be implanted near or within the desired portion of the body to be stimulated such as, for example, the brain, spinal cord, or other body organs or tissues. In one example of operation for deep brain stimulation, access to the desired position in the brain can be accomplished by drilling a hole in the patient's skull or cranium with a cranial drill (commonly referred to as a burr), and coagulating and incising the dura mater, or brain covering. The lead 110 can be inserted into the cranium and brain tissue with the assistance of a stylet (not shown). The lead 110 can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 110, advance the lead 110, retract the lead 110, or rotate the lead 110.

In some embodiments, measurement devices coupled to the muscles or other tissues stimulated by the target neurons, or a unit responsive to the patient or clinician, can be coupled to the implantable pulse generator or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in, for example, tremor frequency or amplitude in response to stimulation of neurons. Alternatively, the patient or clinician can observe the muscle and provide feedback.

The lead 110 for deep brain stimulation can include stimulation electrodes, recording electrodes, or both. In at least some embodiments, the lead 110 is rotatable so that the stimulation electrodes can be aligned with the target neurons after the neurons have been located using the recording electrodes.

Stimulation electrodes may be disposed on the circumference of the lead 110 to stimulate the target neurons. Stimulation electrodes may be ring-shaped so that current projects from each electrode equally in every direction from the position of the electrode along a length of the lead 110. In the embodiment of FIG. 2, two of the electrodes 125 are ring electrodes 120. Ring electrodes typically do not enable stimulus current to be directed from only a limited angular range around of the lead. Segmented electrodes 130, however, can be used to direct stimulus current to a selected angular range around the lead. When segmented electrodes are used in conjunction with an implantable pulse generator that delivers constant current stimulus, current steering can be achieved to more precisely deliver the stimulus to a position around an axis of the lead (i.e., radial positioning around the axis of the lead). To achieve current steering, segmented electrodes can be utilized in addition to, or as an alternative to, ring electrodes.

The lead 100 includes a lead body 110, terminals 135, and one or more ring electrodes 120 and one or more sets of segmented electrodes 130 (or any other combination of electrodes). The lead body 110 can be formed of a biocompatible, non-conducting material such as, for example, a polymeric material. Suitable polymeric materials include, but are not limited to, silicone, polyurethane, polyurea, polyurethane-urea, polyethylene, or the like. Once implanted in the body, the lead 100 may be in contact with body tissue for extended periods of time. In at least some embodiments, the lead 100 has a cross-sectional diameter of no more than 1.5 mm and may be in the range of 0.5 to 1.5 mm. In at least some embodiments, the lead 100 has a length of at least 10 cm and the length of the lead 100 may be in the range of 10 to 70 cm.

The electrodes 125 can be made using a metal, alloy, conductive oxide, or any other suitable conductive biocompatible material. Examples of suitable materials include, but are not limited to, platinum, platinum iridium alloy, iridium, titanium, tungsten, palladium, palladium rhodium, or the like. Preferably, the electrodes are made of a material that is biocompatible and does not substantially corrode under expected operating conditions in the operating environment for the expected duration of use.

Each of the electrodes can either be used or unused (OFF). When the electrode is used, the electrode can be used as an anode or cathode and carry anodic or cathodic current. In some instances, an electrode might be an anode for a period of time and a cathode for a period of time.

Deep brain stimulation leads may include one or more sets of segmented electrodes. Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a radially segmented electrode array ("RSEA"), current steering can be performed not only along a length of the lead but also around a circumference of the lead. This provides precise three-dimensional targeting and delivery of the current stimulus to neural target tissue, while potentially avoiding stimulation of other tissue. Examples of leads with segmented electrodes include U.S. Pat. Nos. 8,473,061; 8,571,665; and 8,792,993; U.S. Patent Application Publications Nos. 2010/0268298; 2011/0005069; 2011/0130803; 2011/0130816; 2011/0130817; 2011/0130818; 2011/0078900; 2011/0238129; 2012/0016378; 2012/0046710; 2012/0071949; 2012/0165911; 2012/197375; 2012/0203316; 2012/0203320; 2012/0203321; 2013/0197424; 2013/0197602; 2014/0039587; 2014/0353001; 2014/0358208; 2014/0358209; 2014/0358210; 2015/0045864; 2015/0066120; 2015/0018915; 2015/0051681; U.S. patent application Ser. Nos. 14/557,211 and 14/286,797; and U.S. Provisional Patent Application Ser. No. 62/113,291, all of which are incorporated herein by reference.

In many instances, it is important to identify the rotational orientation of a lead with segmented electrodes when the lead is implanted into the patient (for example, in the brain of a patient.) Knowing the rotational orientation of the lead (and, in particular, the rotational orientation of the individual segmented electrodes) will facilitate determining which segmented electrodes may be situated for stimulating a particular anatomical or physiological tissue target or determining an expected direction of the electrical stimulation field that can be generated by each of the segmented electrodes. It may be difficult to determine orientation radiologically because the segmented electrodes at least longitudinal position will often overlap in a radiological image.

To facilitate radiological identification of rotational orientation, the lead can include a rotationally asymmetric marker made of different material (for example, a conductive material such as metal) from the lead body so that the marker and lead body are radiologically distinguishable. As explained in more detail below, radiological imaging, such as computed tomography (CT) imaging, can be used to identify the orientation of the lead due to the asymmetry of the marker.

Figure 3:
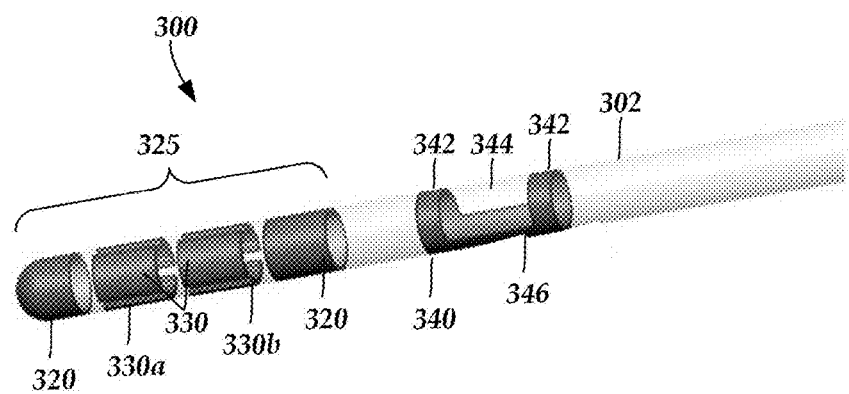
FIG. 3 is a schematic diagram of one embodiment of the distal portion of a lead with an asymmetric marker, according to the invention.

FIG. 3 illustrates one example of a distal portion of a lead 300 with a lead body 302 and electrodes 325 including one or more optional ring electrodes 320 and multiple segmented electrodes 330. The lead 300 also includes a marker 340 that is asymmetrically shaped. The marker 340 is made of a material that is substantially different from the material of the lead body 302, particularly, when viewed using a radiological imaging technique, such as CT imaging, so that the marker is radiologically distinguishable from the lead body. In at least some embodiments, the marker 340 is made of metal (such as a pure metal or an alloy) and, in at least some embodiments, is made of the same material as the electrodes 325.

The marker 340 defines one or more optional rings 342 formed around the entire circumference of the lead 300, at least one window 344, and a longitudinal band 346 disposed opposite the window. In at least some embodiments, the longitudinal band 346 of the marker 340 extends around no more than 80%, 75%, 67%, 60%, 50%, 40%, 34%, 25%, or 20% of the circumference of the lead with the window 344 extending around the remainder of the circumference. To further facilitate the determination of directionality of the marker 340 and ensure that the resulting bulge, described below, will be visible around less than half of the lead, the marker will extend around less than half the circumference of the lead and may extend around no more than one third or one quarter of the circumference. In at least some embodiments, the longitudinal band 346 of the marker 340 is aligned with at least one of the segmented electrodes 330 (such as segmented electrodes 330a, 330b in the illustrated embodiment of FIG. 3.)

The use of an asymmetrical marker 340 on the lead 300 aids in the identification of the rotational orientation of the lead using imaging techniques, such as CT imaging or other radiological imaging techniques. In at least some embodiments, a system or method includes generating or otherwise obtaining radiological images of an implanted lead 300 with an asymmetric marker 340 that will aid a clinician in making a determination of the rotational orientation of the lead. In at least some embodiments, determining the rotational orientation of the lead can also aid in determining the location of the segmented electrodes relative to anatomical or physiological structures of interest (for example, structures in the brain, spinal cord, or other patient tissues). In at least some embodiments, display of information from one or more radiological (e.g., CT) images in the form of an isosurface image can be used to identify the rotational orientation of the lead 300 using the marker 304. For example, the asymmetric marker 340 of the lead 300 can produce a bulge in an appropriately selected CT isosurface that forms in the direction of the longitudinal band 346 of the marker.

An isosurface image from CT image (or other radiological image) data can be generated, for example, by combining image data from a series of slices and then selecting those portions of the combined image that have the same intensity (or fall within the same narrow band of intensities) or other image parameter. In the example of CT imaging, the intensity is often related to the absorption of x-rays by the material being imaged. For example, a marker 340 made of metal will typically have a higher absorption of x-rays than the lead body 302, which is formed of a polymeric material, resulting in different, and distinguishable, intensities for these components in a CT image. An isosurface image, generated from the corresponding CT images by selecting a single intensity or narrow band of intensities, can be used to identify those portions of the lead that are formed of metal, such as the marker 340.

As an example, FIGS. 4A and 4B illustrate isosurface images from CT scans of a lead with segmented electrodes and an asymmetric marker. In the FIG. 4A, the lead was aligned along the scanner axis and, in FIG. 4B, the lead was aligned at an angle to the scanner axis. The intensities in this CT scan are coded in the standard Hounsfield Units (HU) which in these examples ranges from −1024 to +3072. In this particular example, the isosurface image was drawn at 2000 HU. The slice thickness was 0.6 mm and adjacent slices had 50% overlap.

A distinct bulge 452 of the isosurface in the marker portion is apparent in both isosurface images. FIGS. 4A and 4B clearly show that the lead marker portion appears to be anisotropic i.e. it has a specific direction. In particular, the metal band of the marker appears as a bulge in the isosurface and the opposite side, which corresponds to the absence of metal, does not exhibit this bulge in the isosurface.

FIGS. 5A and 5B illustrate the isosurface images for the leads of FIGS. 4A and 4B, respectively, restricted to the marker portion. The isosurface images were generated by resampling the CT data on an isotropic grid aligned with the lead axis, with voxel size 0.1 mm in each direction. Resampling on a grid aligned with the lead axis can facilitate visualization of features that may not be as apparent when the CT slices are aligned at an angle to the lead axis. Resampling on a finer grid may also facilitate visualization. The bulge 452 corresponding to the position of the longitudinal band 346 of the lead marker 340 is clearly observed. In addition, there is a dent on the marker portion between the bulge of the longitudinal band (right portion of the isosurfaces in FIGS. 5A and 5B) and the window (left portion of the isosurfaces in FIGS. 5A and 5B).

Figure 6:
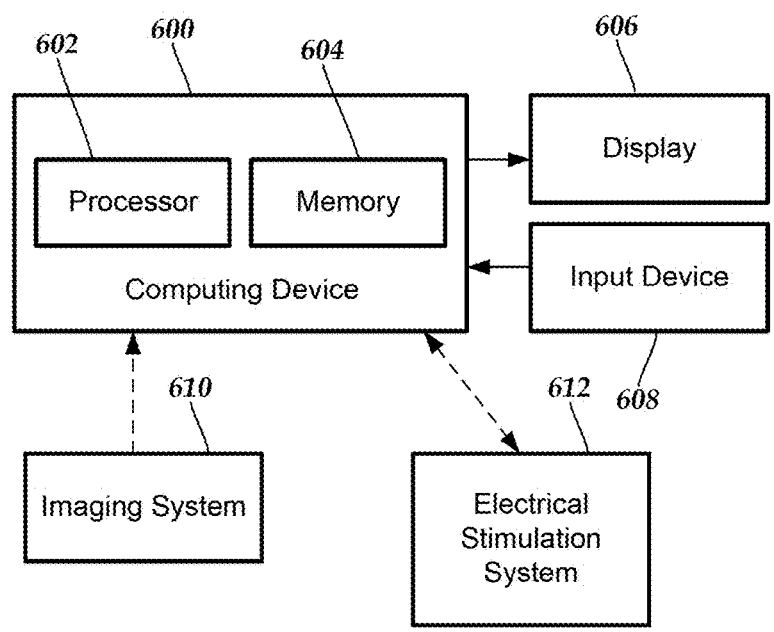
FIG. 6 is a schematic block diagram of one embodiment of a system for determining rotational orientation of a lead, according to the invention.

FIG. 6 illustrates one embodiment of a system for practicing the invention. The system can include a computing device 600 or any other similar device that includes a processor 602 and a memory 604, a display 606, an input device 608, and, optionally, the electrical stimulation system 612 (such as the system 10 in FIG. 1). The system 600 may also optionally include one or more imaging systems 610 (for example, a CT imaging system). In some embodiments, the computing device 600 is part of the imaging system 610. In some embodiments, the computing device 600 is part of the electrical stimulation system 612, such as part of the clinician programmer 18 (FIG. 1), remove control 16 (FIG. 1), or external trial stimulator 20 (FIG. 1). In other embodiments, the computing device 600 is not part of either the electrical stimulation system 612 or imaging system 610.

The computing device 600 can be a computer, tablet, mobile device, or any other suitable device for processing information. The computing device 600 can be local to the user or can include components that are non-local to the computer including one or both of the processor 602 or memory 604 (or portions thereof). For example, in some embodiments, the user may operate a terminal that is connected to a non-local computing device. In other embodiments, the memory can be non-local to the user.

The computing device 600 can utilize any suitable processor 602 including one or more hardware processors that may be local to the user or non-local to the user or other components of the computing device. The processor 602 is configured to execute instructions provided to the processor.

Any suitable memory 604 can be used for the computing device 602. The memory 604 illustrates a type of computer-readable media, namely computer-readable storage media. Computer-readable storage media may include, but is not limited to, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display 606 can be any suitable display device, such as a monitor, screen, display, or the like, and can include a printer. The input device 608 can be, for example, a keyboard, mouse, touch screen, track ball, joystick, voice recognition system, or any combination thereof, or the like.

One or more imaging systems 610 can be used including, but not limited to, MRI, CT, ultrasound, or other imaging systems. The imaging system 610 may communicate through a wired or wireless connection with the computing device 600 or, alternatively or additionally, a user can provide images from the imaging system 610 using a computer-readable medium or by some other mechanism.

The electrical stimulation system 612 can include, for example, any of the components illustrated in FIG. 1. The electrical stimulation system 612 may communicate with the computing device 600 through a wired or wireless connection or, alternatively or additionally, a user can provide information between the electrical stimulation system 612 and the computing device 600 using a computer-readable medium or by some other mechanism. In some embodiments, the computing device 600 may include part of the electrical stimulation system, such as, for example, the IPG, CP, RC, ETS, or any combination thereof.

One or more images or imaging data, for example, CT images or imaging data, can be provided to, or generated by, the computing device 600 and the computing device can produce an isosurface image, as illustrated in FIGS. 4A-5B. The images or imaging data can be provided by the imaging system 610 or any other suitable image source. Alternatively, the isosurface image can be provided to the computing device 600 from the imaging system 610 or any other suitable source.

In at least some embodiments, the computing device 600 displays the isosurface image on the display 606. The isosurface image may be based on a user-specified isovalue (or narrow range around the user-specified isovalue) or may be based on a default or predefined isovalue (or narrow range around the isovalue). In some embodiments, the computing device 600 provides a user interface for receiving the user-specified isovalue as an input. In some embodiments, the user interface can include a slider bar, or other mechanism, that allows the user to change the isovalue and see the resulting isosurface image. In at least some embodiments, at low isovalues voxels corresponding to the skull and the brain may be included in the isosurface image. In at least some embodiments, to avoid this, the system may require that the user-specified isovalue meet or exceed a threshold (for example, a threshold of 1000 or 30% of the peak Hounsfield unit or any other suitable value).

In at least some embodiments, the orientation of the marker 340 is more discernible in the isosurface image when the marker is viewed from certain angles. In at least some embodiments, the computing device 600 includes a user interface that has one or more controls to allow the user to rotate the isosurface around one or more axes. Such controls can include, for example, clockwise or counterclockwise (or other) rotational controls, as well as axis selection controls. In some embodiments, the user interface allows the user to rotate the isosurface around one, two, three of the coordinate axes, such as the coordinate axes illustrated in FIGS. 4A-5B. FIG. 7A illustrates the isosurface image of FIG. 5A rotated about an axis and FIG. 7B illustrates the isosurface image of FIG. 5A rotated for top-down view with the longitudinal axis of the lead forming a point in the image. In some embodiments, the user interface allows the user to rotate the isosurface about the longitudinal axis of the lead. In some embodiments, other axes of rotation may also be selected or the user may be allowed to define an axis of rotations. In some embodiments, the user interface has a control (such as a play button) that will continuously rotate the lead around the longitudinal axis of the lead and may optionally include a control to modify the speed of the rotation. In some embodiments, the computing device 600 may allow display of more than one isosurface image (for example, the isosurface image at different angles) so that the user can compare the images. In some embodiments, the computing device 600 may include one or more controls that display the isosurface image at predetermined orientations (for example, a control to produce a top-down view (for example, FIG. 7B) of the isosurface image or a control to produce an edge-on view (for example, FIGS. 4A-5B and 7A)).

In some embodiments, the computing device 600 includes a user interface with lead orientation controls that allow the user to define a direction on the isosurface, for example, a direction that corresponds, in the user's opinion, to the longitudinal band 346 of the marker 340. For example, the computing device can provide the user with two orientation axes 760, 762, as illustrated in FIGS. 7A and 7B. In at least some embodiments, these orientation axes can be centered on the marker midpoint and with, for example, one orientation axis 760 along the longitudinal axis of the lead. The computing device 600 may select the second orientation axis 762 or may permit the user to select the second orientation axis. In at least some embodiments, the user can rotate or otherwise move the second orientation axis to align the second axis with the bulge 452 corresponding the longitudinal band 346 of the marker 340. In some embodiments, the computing device 600 may determine an initial orientation of the second orientation axis 762 based on analysis of the original images or imaging data or analysis of the isosurface image (or analysis of any combination of the original images, imaging data, or isosurface image) and place the second orientation axis 762 in that initial orientation on the display device.

In some embodiments, the user interface includes one or more controls that allow the user to utilize the lead isosurface image to manually assign one or more of the location of the lead tip, the location of the lead shaft, the location of one or more electrodes (including segmented electrodes), or any combination thereof.

In some embodiments, the user interface can utilize the images and the identification of the position of the longitudinal band of the marker to then depict the location and orientation of the lead (as, for example, a model of the lead that optionally includes models of the lead electrodes). In at least some embodiments, the user interface may also depict the location and orientation of the lead with respect to anatomical or physiological structures. In some embodiments, the user interface may include controls to provide calculated distances between the different electrodes of the leads and anatomical or physiological structures (for example, brain structures) in the image once the lead marker orientation is determined. Such calculations and depictions may utilize additional images (such as CT or Mill images) to identify or infer locations of the anatomical or physiological structures. The user interface may also include tools may also be provided for measuring distances (for example, a distance between an electrode and a point in the imaged anatomy) using, for example, a ruler or lines. In at least some embodiments, the user interface can also include controls to display the original images (e.g., CT images) from which the isosurface image is derived or additional images obtained or generated from an imaging system. The identification of anatomical and physiological structures is discussed in at least U.S. Pat. Nos. 8,326,433; 8,675,945; 8,831,731; 8,849,632; and 8,958,615; U.S. Patent Application Publications Nos. 2009/0287272; 2009/0287273; 2012/0314924; 2013/0116744; 2014/0122379; and 2015/0066111; and U.S. Provisional Patent Application Ser. No. 62/030,655, all of which are incorporated herein by reference in their entirety.

In at least some embodiments, the user interface may include controls to allow the user to zoom onto any selected portion of the lead, including the marker, within the isosurface image or zoom away from the lead to obtain a view of a larger portion of the lead in the isosurface image. This may facilitate observation of the marker shape.

In addition, the user interface may include one or more of the following: a control for resampling the image data on a finer grid; a control to align the lead axis with one of the coordinate axes (or this may be performed automatically as a default); a control to change lighting or color or both to make the isosurface shape more discernible, or any combination of these and the other controls described herein.

Figure 8:
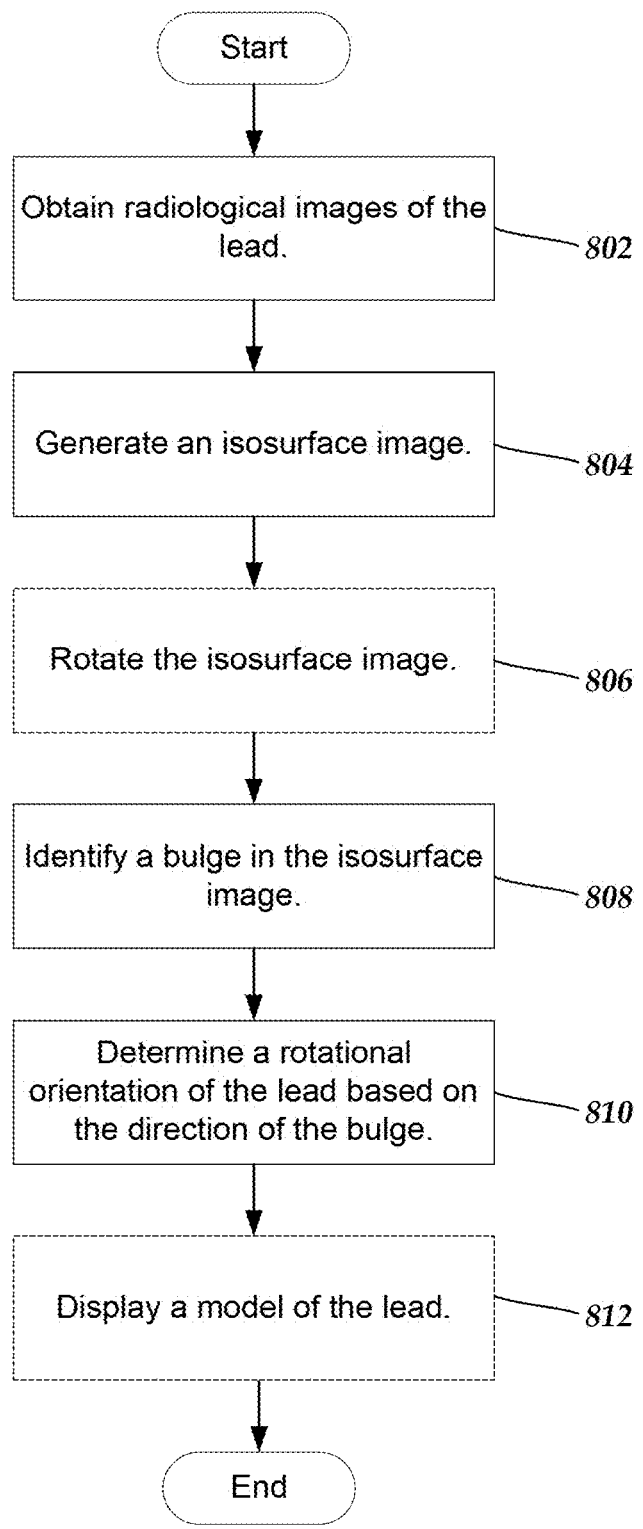
FIG. 8 is a flowchart of one embodiment of a method of determining rotational orientation of a lead, according to the invention.

FIG. 8 illustrates one method of determining the rotational orientation of a lead, such as lead 300. In step 802, radiological images of the lead are obtained. The lead has an asymmetric marker as described above. In step 804, an isosurface image is generated from the radiological images and displayed on a display device. In optional step 806, the isosurface image can be rotated on the display. In step 808, a bulge in the isosurface image corresponding the longitudinal band of the marker is identified. In step 810, a rotational orientation of the lead is determined based on the direction of the bulge in the isosurface image. In optional step 812, a model of the lead is displayed based on the determined rotational orientation. The steps of this method may be modified to incorporate any of the other features of the computing device or user interface described above. Steps of this method can be performed by the computing device and, in some instances, in response to user input or command.

In the embodiments described above, the marker 340 is not an electrode and is not electrically coupled to any of the terminals at the proximal end of the lead 300. In other embodiments, however, the marker can be an electrode and electrically coupled to one of the terminals. Such an electrode may have the form illustrated in FIG. 3 or a form without one or both of the optional rings 342. In other embodiments, one or more of the segmented electrodes 330 can have a different shape (for example, can be larger) from the other segmented electrodes (for example, different from segmented electrodes in the same set at a particular longitudinal position or different from all of the other segmented electrodes) so that there is a visible distinction in the isosurface image due to the asymmetry between the segmented electrodes. For example, one segmented electrode may be substantially larger (for example, at least 25%, 50%, 75%, 100%, 150%, or 200% larger) than the other segmented electrodes or all segmented electrodes along one side of the lead may be substantially larger (for example, at least 25%, 50%, 75%, 100%, 150%, or 200% larger) than the other segmented electrodes. Any other asymmetry between segmented electrodes that can be visually identified in the isosurface may be suitable for identifying the rotational orientation of the lead by the methods and systems described herein.

The methods and systems described herein may be embodied in many different forms and should not be construed as limited to the embodiments set forth herein. Accordingly, the methods and systems described herein may take the form of an entirely hardware embodiment, an entirely software embodiment or an embodiment combining software and hardware aspects. Systems referenced herein typically include memory and typically include methods for communication with other devices including mobile devices. Methods of communication can include both wired and wireless (e.g., RF, optical, or infrared) communications methods and such methods provide another type of computer readable media; namely communication media. Wired communication can include communication over a twisted pair, coaxial cable, fiber optics, wave guides, or the like, or any combination thereof. Wireless communication can include RF, infrared, acoustic, near field communication, Bluetooth™, or the like, or any combination thereof.

It will be understood that each of the methods disclosed herein, can be implemented by computer program instructions. These program instructions may be provided to a processor to produce a machine, such that the instructions, which execute on the processor, create means for implementing the actions specified in the flowchart block or blocks disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

The above specification provides a description of the structure, manufacture, and use of the invention. Since many embodiments of the invention can be made without departing from the spirit and scope of the invention, the invention also resides in the claims hereinafter appended.

What is claimed as new and desired to be protected by Letters Patent of the United States is:

1. A method for identifying a rotational orientation of an implanted electrical stimulation lead, the method comprising:
    obtaining a plurality of radiological images of the lead, the lead comprising a lead body, a plurality of segmented electrodes disposed along a distal portion of the lead body, and an asymmetric marker disposed along the distal portion of the lead body and comprising a longitudinal band that extends around a portion of a circumference of the lead body and defines a marker window extending around a remainder of the circumference of the lead body and opposite the longitudinal band, wherein the asymmetric marker and lead body are formed of different materials that are distinguishable from each other in the radiological images, wherein each segmented electrode extends around no more than 50% of a circumference of the lead body;
    generating an isosurface image from the plurality of radiological images and displaying the isosurface image on a display device, wherein the isosurface image comprises an image of the longitudinal band of the marker;
    identifying a bulge in the isosurface image corresponding the longitudinal band of the marker; and
    determining a rotational orientation of the lead based on a rotational orientation of the bulge in the isosurface image.

2. The method of claim 1, further comprising displaying, on the display device, a model of at least the distal portion of the lead body oriented along the determined rotational orientation.

3. The method of claim 2, wherein displaying a model comprises displaying the model of at least the distal portion of the lead body and including models of the segmented electrodes of the lead.

4. The method of claim 1, further comprising rotating the isosurface image on the display device in response to a user command.

5. The method of claim 4, wherein rotating the isosurface image comprises continuously rotating the isosurface image in response to a user command and stopping the rotation in response to a user command.

6. The method of claim 4, wherein rotating the isosurface image comprises rotating the isosurface image about an axis selected by the user.

7. The method of claim 1, wherein determining a rotational orientation comprises placing an orientation axis on the isosurface image on the display device in response to a user command.

8. The method of claim 7, further comprising modifying a direction of the orientation axis in response to user input.

9. The method of claim 1, further comprising receiving an isovalue from a user input and generating another isosurface image based on the isovalue.

10. A system for identifying a rotational orientation of an implanted electrical stimulation lead, the system comprising:
    a display device; and a computer processor coupled to the display device and configured and arranged to perform the following actions:

receiving a plurality of radiological images of the lead, the lead comprising a lead body, a plurality of segmented electrodes disposed along a distal portion of the lead body and an asymmetric marker disposed along the distal portion of the lead body, and comprising a longitudinal band that extend around a portion of a circumference of the lead body and defines a marker window extending around a remainder of the circumference of the lead body and opposite the longitudinal band, wherein the asymmetric marker and lead body are formed of different materials that are distinguishable from each other in the radiological images, wherein each segmented electrode extends no more than 50% of a circumference of the lead body;

generating an isosurface image from the plurality of radiological images, wherein the isosurface image comprises an image of the longitudinal band of the marker;

displaying the isosurface image on the display device;

in response to a user command, rotating, on the display device, the isosurface image about at least one axis;

in response to a user command, displaying, on the display device, a user-selected orientation axis on the isosurface image; and in response to a user command, displaying, on the display device, a model of at least the distal portion of the lead body oriented along the orientation axis.

11. The system of claim 10, wherein the actions further comprise, in response to user input of an isovalue, generating another isosurface image based on the isovalue.

12. The system of claim 11, wherein the actions further comprise displaying, on the display device, a slider control which the user can operate to input the isovalue.

13. The system of claim 10, wherein the actions further comprise, in response to a user command, zooming into the isosurface image on the display device to magnify a portion of the isosurface image.

14. The system of claim 10, wherein rotating the isosurface image comprises continuously rotating the isosurface image in response to a user command and stopping the rotation in response to a user command.

15. The system of claim 10, wherein rotating the isosurface image comprises rotating the isosurface image comprises rotating the isosurface image about an axis selected by the user.

16. The system of claim 10, wherein the actions further comprise displaying, on the display device and relative to the model, at least one anatomical or physiological structure.

17. The system of claim 16, wherein the actions further comprise displaying, on the display, a calculated distance between at least one of the segmented electrodes of the lead and a one of the at least one anatomical or physiological structure.

18. The system of claim 10, further comprising the lead.

19. The system of claim 10, wherein the actions further comprise, in response to a user command, modifying, on the display device, a direction of the orientation axis.

20. A computer-implemented method, the method comprising:

receiving a plurality of radiological images of a lead, the lead comprising a lead body, a plurality of segmented electrodes disposed along a distal portion of the lead body, and an asymmetric marker disposed along the distal portion of the lead body and comprising a longitudinal band that extend around a portion of a circumference of the lead body and defines a marker window extending around a remainder of the circumference of the lead body and opposite the longitudinal band, wherein the asymmetric marker and lead body are formed of different materials that are distinguishable from each other in the radiological images, wherein each segmented electrode extends around no more than 50% of a circumference of the lead body;

generating an isosurface image from the plurality of radiological images, wherein the isosurface image comprises an image of the longitudinal band of the marker;

displaying the isosurface image on the display device;

in response to a user command, rotating, on the display device, the isosurface image about at least one axis;

in response to a user command, displaying, on the display device, a user-selected orientation axis on the isosurface image; and in response to a user command, displaying, on the display device, a model of at least the distal portion of the lead body oriented along the orientation axis.

* * * * *